United States Patent
Cantillon et al.

(10) Patent No.: US 12,268,507 B2
(45) Date of Patent: Apr. 8, 2025

(54) DISPOSABLE ECG ELECTRODES ADAPTED TO REDUCE LEADS-OFF EVENTS

(71) Applicant: The Cleveland Clinic Foundation, Cleveland, OH (US)

(72) Inventors: Daniel Cantillon, Hudson, OH (US); Marc Petre, Shaker Heights, OH (US); Shengqiang Gao, Beachwood, OH (US); Torey Hovest, Copley, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 729 days.

(21) Appl. No.: 17/510,699

(22) Filed: Oct. 26, 2021

(65) Prior Publication Data

US 2022/0133202 A1     May 5, 2022

Related U.S. Application Data

(60) Provisional application No. 63/108,467, filed on Nov. 2, 2020.

(51) Int. Cl.
| | |
|---|---|
| *A61B 5/274* | (2021.01) |
| *A61B 5/00* | (2006.01) |
| *A61B 5/257* | (2021.01) |
| *A61B 5/28* | (2021.01) |

(52) U.S. Cl.
CPC .............. *A61B 5/274* (2021.01); *A61B 5/257* (2021.01); *A61B 5/28* (2021.01); *A61B 5/6833* (2013.01); *A61B 2562/225* (2013.01)

(58) Field of Classification Search
CPC ........... A61B 5/274; A61B 5/28; A61B 5/257; A61B 5/6833; A61B 2562/225
See application file for complete search history.

(56) References Cited

U.S. PATENT DOCUMENTS

| | | | |
|---|---|---|---|
| 6,453,186 B1 * | 9/2002 | Lovejoy ................ | A61B 5/282 600/386 |
| 9,451,897 B2 * | 9/2016 | Mazar ................... | A61B 5/6833 |
| 2002/0133069 A1 * | 9/2002 | Roberts ................. | A61B 5/282 600/382 |
| 2006/0258969 A1 | 11/2006 | Brown et al. | |

(Continued)

FOREIGN PATENT DOCUMENTS

CN      202553929 U      11/2012

OTHER PUBLICATIONS

3M™ Red Dot™ ECG Monitoring Electrodes, Pre-Wired, 2289PAL. 2 pages. Retrieved from the Internet on Oct. 28, 2021 via website: https://www.3m.com/3M/en_US/p/d/v000154429/1/.

*Primary Examiner* — Linda C Dvorak
*Assistant Examiner* — Abigail Bock
(74) *Attorney, Agent, or Firm* — Tucker Ellis LLP

(57) ABSTRACT

ECG electrode assemblies are disclosed which include an adhesive-backed patch incorporating an ECG electrode and an adhesive-backed cover configured to cover and surround a lead wire clip attached to a contact of the ECG electrode. ECG electrode assemblies comprising said adhesive-backed patch and said adhesive-backed cover secure the connection between the lead and the electrode and effectively reduce the number of telemetry disruptions due to leads failure. ECG electrode assemblies can also provide water resistance to allow for patient showering while hospitalized on telemetry monitoring.

22 Claims, 8 Drawing Sheets

(56) References Cited

U.S. PATENT DOCUMENTS

| | | |
|---|---|---|
| 2009/0318793 A1 | 12/2009 | Datta et al. |
| 2010/0081913 A1* | 4/2010 | Cross ............... A61B 5/282 |
| | | 600/509 |
| 2016/0029906 A1 | 2/2016 | Tompkins et al. |
| 2017/0258402 A1* | 9/2017 | Acquista ............ H01R 31/00 |
| 2019/0022400 A1* | 1/2019 | Kumar ............... A61B 5/361 |
| 2020/0054285 A1* | 2/2020 | Lemons ............. A61N 1/0492 |

* cited by examiner

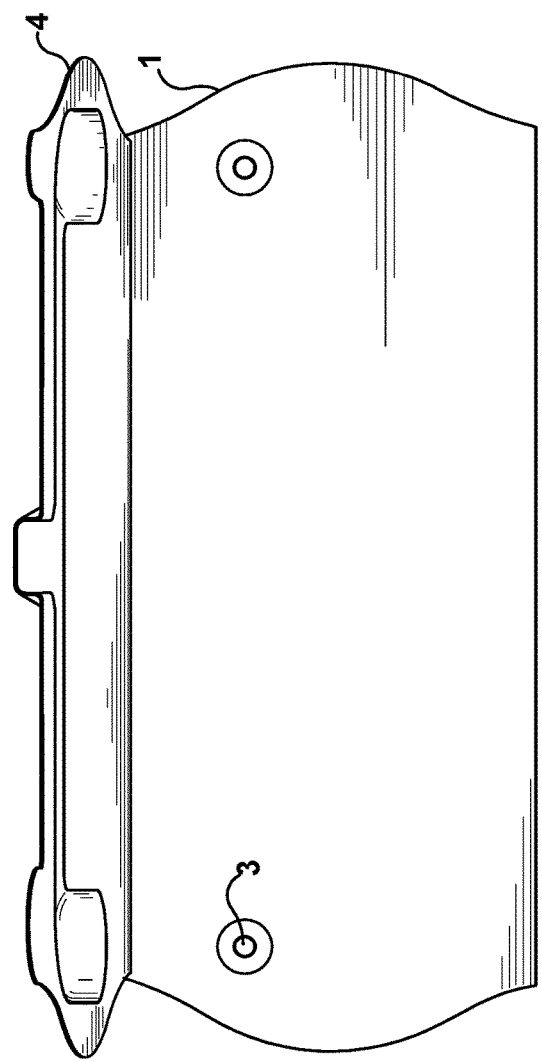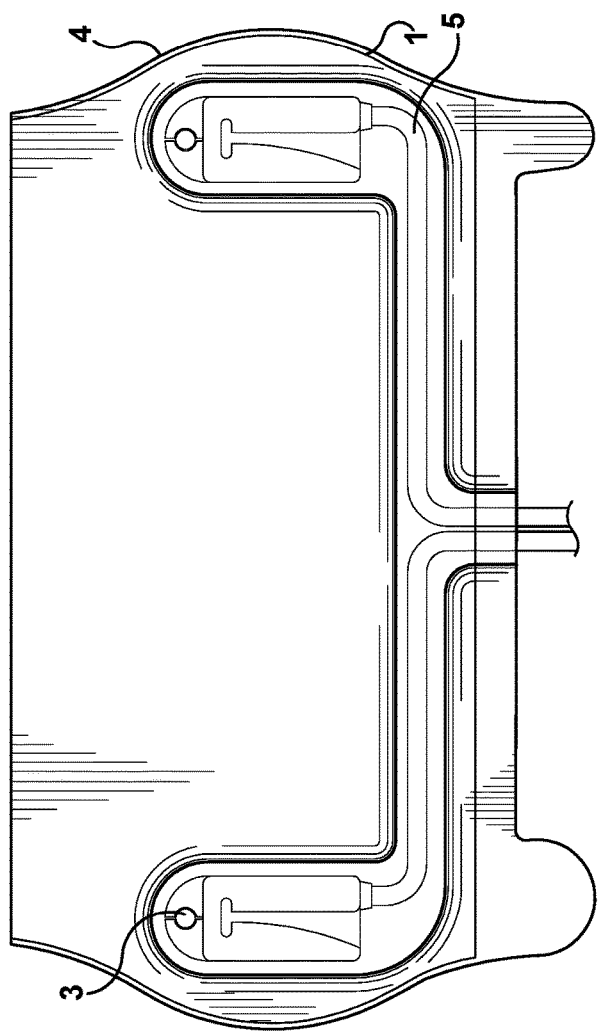
FIG. 5A
FIG. 5B

DISPOSABLE ECG ELECTRODES ADAPTED TO REDUCE LEADS-OFF EVENTS

This application claims the benefit of U.S. provisional application Ser. No. 63/108,467 filed Nov. 2, 2020, the contents of which are incorporated herein in their entirety by reference.

TECHNICAL FIELD

This application relates generally to ECG assemblies for reducing telemetry disruptions due to LEADS OFF events.

BACKGROUND

Lead failures account for the overwhelming majority of telemetry monitoring disruptions in multiple clinical studies. This results in a high volume of clinically unactionable alarms while leaving patients vulnerable to undetected arrhythmias. This phenomenon is referred to as alarm fatigue and has been linked to adverse clinical outcomes including death. It also has been identified by multiple professional bodies as a top patient safety concern, including by the Joint Commission, the Emergency Care Research Institute (ECRI), the American Association of Critical Care Nurses and the Society of Hospital Medicine. According to the American Heart Association, in 2016 fewer than 1 in 4 adults survived an in-hospital cardiac arrest, while prior studies have shown that >90% of clinical alarms generated are unactionable, and up to 44% of cardiac arrests are not detected appropriately.

Traditional disposable ECG electrodes are constructed of fabric, foam, or plastic patches with skin adhesive surrounding a central electrode (typically a $Ag^+/Ag^+Cl^-$ gel suspended in an open-cell foam). A metallic button in contact with the electrode is provided for attaching ECG lead wires via a button or clip on the end of a wire of the reusable lead set.

Electrodes designed in this manner frequently become disconnected either through loss of adhesion to the skin, or clip disconnection from the lead wires resulting in a "LEADS OFF" patient monitoring alert. Although the majority of these alerts are technical malfunctions that are not indicative of an issue with the patient, they must be responded to as critical alerts because they result in an unmonitored patient that is vulnerable to clinically-relevant arrhythmias going undetected.

In light of the above, there is a need for a system that improves retention of the lead wire clip to the button contact of an ECG electrode to reduce the number of telemetry disruptions due to LEADS OFF failure while providing a water-resistant elastomeric barrier sufficient to allow patient showering and ambulation while on monitor.

BRIEF DESCRIPTION OF FIGURES

FIG. 5A illustrates a top view of a second embodiment of disposable ECG electrode assembly, similar to the first embodiment, but wherein the adhesive-backed patch has multiple button connectors for a plurality of independent electrodes.

FIG. 5B illustrates the second embodiment after the cover layer has been placed over respective lead wire clips connected to the button connectors, and secured to the adhesive-backed patch.

SUMMARY

There is provided an ECG electrode assembly including a patch and a cover. The patch incorporates an ECG electrode. The cover is configured to cover and surround a lead wire clip attached to a contact of the ECG electrode at a top surface of the patch.

In a further aspect, there is provided an ECG electrode assembly including a patch incorporating a first ECG electrode and a second ECG electrode. A first cover is configured to cover and surround a first lead wire clip attached to a first electrode contact of the first ECG electrode. A second cover is configured to cover and surround a second lead wire clip attached to a second contact of the second ECG electrode.

There is also provided a cover having a bottom surface and a top surface. An adhesive is disposed on the bottom surface. The cover also defines a recess that is open from the bottom surface and is dimensioned to accommodate a lead wire clip attached to a contact of an ECG electrode when the bottom surface of the cover is adhered to a patch that includes the contact.

DESCRIPTION

Figure 1A:
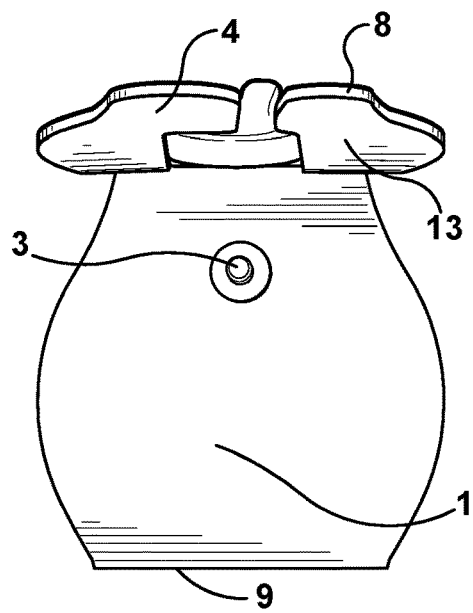
FIG. 1A illustrates a top view of a first embodiment of a disposable ECG electrode assembly having a cover layer separated from an adhesive-backed patch.

Embodiments of a disposable ECG electrode assembly have a (typically foam, but also possibly a solid gel layer or other plastic layer) patch including an ECG electrode and a skin-compatible adhesive to affix the patch to a patient in-use, and a cover. The cover can be a layer adhered over a top surface of the patch, opposite that where the electrode in the patch contacts the patient. When adhered at the top surface, the cover surrounds and preferably encloses a lead wire clip connected to an electrode contact at that top surface. As used herein, the term 'lead wire clip' refers to an element at the terminal end of a lead wire that is configured to interface with an electrode contact at the top surface of the patch, in order to provide electrical communication between the ECG electrode and the lead wire. In conventional embodiments (e.g. as seen in FIG. 1A), the electrode contact is in the form of a male button connector 3 provided at the top surface of the patch 1. To provide communication with a lead wire 5 (see FIG. 1B), a lead wire clip 7 at its terminal end is affixed (e.g. via a snap-fit connection) to the button connector 3 in a conventional manner. In this regard, the lead wire clip 7 can include a plastic housing that receives the terminal end of the lead wire 5 and has a complementary (i.e. female) button connector configured to interface with and snap-fit to the male button connector 3 on the patch 1. Other configurations of the wire clip 7 are known and could be used, the only requirement being that it is adapted to be fitted to and establish electrical communication with an electrical contact of the ECG electrode in the patch 1; such as a button connector 3. For example, the wire clip 7 could be simply a female button connector wired to the terminal end of the lead wire 5 and adapted to complementarily mate with male button connector 3.

As noted above, lead wires having lead wire clips affixable to electrode contacts (e.g. button connectors) on an ECG patch are known. In embodiments of the disclosed ECG electrode assembly, the cover improves retention of the lead wire clip to the patch while providing a preferably water-resistant and optionally elastomeric barrier that sufficiently shields the lead wire clip and its electrical connection to the electrode contact to allow patient showering while on monitor.

The disclosed disposable ECG electrode assembly helps address a major patient safety concern affecting hospital systems and can improve clinical outcomes for hospitalized patients by reducing the number of telemetry disruptions due to LEADS OFF failures. It can also improve patient experience by providing water resistance to allow patient showering while hospitalized on telemetry monitoring.

Figure 1B:
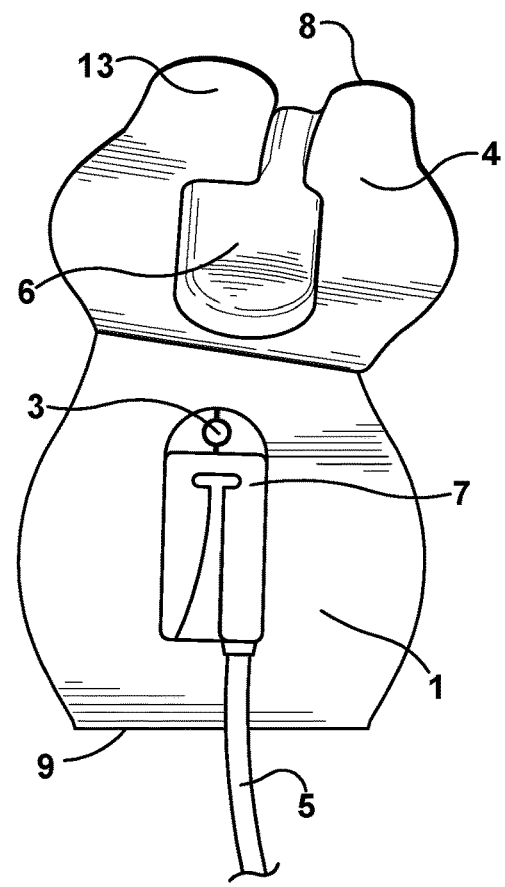
FIG. 1B illustrates a top view of the embodiment in FIG. 1A after a connection has been established between a button connector of an electrode on the patch and a lead wire clip.
Figure 1C:
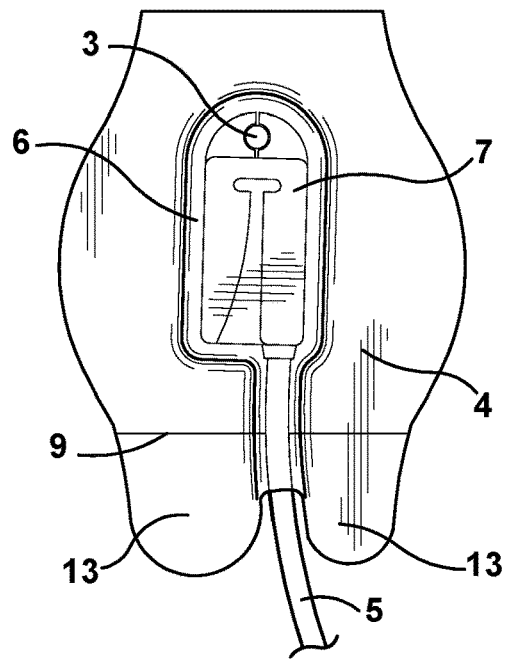
FIG. 1C illustrates a top view of the embodiment in FIG. 1A after the cover layer has been placed over the connected lead wire clip and secured around it to the adhesive-backed patch.

In a first embodiment of the disposable ECG electrode assembly illustrated in FIGS. 1A-1C, the disposable ECG electrode assembly includes a patch 1 incorporating an ECG electrode 2 and an electrode contact (which can be in the form of a button connector 3) in electrical communication with the electrode 2. The electrode 2 (see FIGS. 2A, 2B) typically is embedded in the patch 1 and adapted so that it can be placed in electrical communication with the patient's skin (typically via a conductive gel) when the patch is adhered to the skin. The patch 1 includes or is coated with skin-compatible adhesive on its bottom surface for affixation thereof to a patient's skin in-use. The ECG electrode assembly also includes an adhesive-backed cover (e.g. cover layer 4) configured to cover and surround a lead wire clip 7 attached to the button connector 3 at the top surface of the patch 1. In this manner, the adhesive-backed patch 1 incorporating the ECG electrode 2 provides an electrical connection between the lead wire 5 and the patient when the bottom surface of the adhesive-backed patch 1 is applied to the skin of the patient.

In one instance, the adhesive-backed cover layer 4 and the patch 1 may be separate components. In another instance, they may be connected together, for example, hinged together via a seam between adjacent to respective edges of each. In the case of a plastic cover layer 4, the cover layer 4 may be plastic welded to the top surface of the patch 1, which also can be made of plastic (e.g. a plastic foam). In another instance, the adhesive-backed cover layer 4 may be integrally formed with the patch 1 such that the cover layer 4 and the patch 1 form a single component. For example, the patch 1 may be formed as a plastic element having an integral flap that serves as the cover layer 4 and which need not be separately adhered in an additional step. However configured, the cover layer 4 has a bottom surface that can be provided with adhesive and is adapted to cover and be adhered to the top surface of the patch 1. The top surface of the cover layer 4 may be smooth, or it may be textured to improve the user's grip on the cover layer 4 during application or removal. When the bottom surface of the cover layer 4 is adhesive-coated, the assembly may be supplied initially with a disposable release liner disposed over the adhesive on that surface. The disposable release liner may be removed to expose the adhesive in-use, so that the cover layer 4 can be adhered over the top surface of the subjacent patch 1.

The cover layer 4 can be made of a water-resistant material in order to present a water barrier to the lead wire clip 7 underneath in-use. The adhesive used to affix the cover layer 4 to the patch 1 preferably is a water-resistant pressure-sensitive adhesive (PSA) adapted to provide a water-resistant barrier surrounding the lead wire connector 7 when it is attached to the button connector 3 and covered by the cover layer 4. In this manner, the connection between the lead wire 5 and the button connector 3 of the electrode 2 is isolated between the cover layer 4 and the patch 1 via a substantially water-tight seal provided by the intermediate adhesive, enabling the patient to shower throughout continuous telemetry-monitoring.

The water-resistant PSA adhesives for use with the cover layer 4 can be selected from any conventional or otherwise suitable adhesives. Other suitable attachment modalities (e.g., tacky adhesion or cohesion between adjacent surfaces) also may be used in lieu of an adhesive. For example, the cover layer 4 may be made of the same material as the patch 1, wherein the top surface of the patch 1 and the bottom surface of the cover layer 4 possess sufficient surface energy as to provide a robust attachment between them based on their inherent tack, preferably that will present a level of resistance to water intrusion. Alternatively, they may be made of different materials whose opposing and contacting surfaces have been appropriately adapted to present similarly robust adhesion therebetween without the need for an additional adhesive. Such surface-to-surface tacky adhesion modalities may benefit from being more easily reversible in case it becomes desired to remove the lead wire (e.g. temporarily) from the electrode assembly. However, they may yield a less robust water-tight seal than a conventional water-resistant PSA adhesive. Indeed, water-resistant PSA adhesives also may be used to provide reversible attachment between the cover layer and the patch if desired. In this case, the particular adhesive preferably will be a removable water-resistant PSA adhesive, selected to provide adequate tack to ensure acceptable adhesion between the cover layer and the patch, but which is removable and re-placeable to re-attach the cover layer to the patch.

As described above, the cover layer 4 is configured to provide a water-tight seal surrounding the lead wire clip 7 where it connects to the electrode contact (e.g. button connector 3). However, in other embodiments water-tightness may not be required; e.g. where it will not be desirable or necessary to shower while on telemetry. In such instances, other sealing modalities that are not necessarily water-tight may be utilized, such as conventional hook-and-loop (e.g. Velcro®) fasteners wherein either the hook- or loop element of such conventional fasteners are provided (e.g. as a layer or strip) on the cover-layer surface, and the other of the hook- or loop elements is provided (e.g. as a layer or strip) on the patch surface, so that when brought into contact they will cooperate to affix the cover layer to the patch. Such an embodiment still will be effective to cover and protect the lead wire clip 7 in-use when attached to the electrode contact of the patch, and will provide other benefits described herein—e.g. protection against tearing away the lead wire clip 7 when the wire 5 is snagged in-use. Although hook-and-loop fasteners are noted above, any conventional or suitable cooperative fastener system can be used adhere the cover layer to the patch in-use.

The cover layer 4 may have a recess 6 configured to accommodate the lead wire clip 7 connected to the lead wire 5 when affixed to the button connector 3, as shown in FIGS. 1B and 1C. The recess 6 helps define a cavity complementary to the underlying lead wire clip 7, wherein the surrounding portion of the cover layer 4 can be affixed to the top surface of the patch 1 in order to isolate the lead wire clip 7 therebetween. This facilitates a more secure connection between the lead wire clip 7 and the button connector 3 and promotes water-resistance by enclosing those components in a bound cavity defined by the cover layer 4 and sealed via a surrounding water-resistant adhesive (or adhesive/cohesive seal) between the cover layer 4 and the patch 1.

If it is desired to reversibly expose the button connector 3 for successive removal and re-attachment of the lead wire clip 7, then the cover layer 4 can incorporate pull tabs 13, as illustrated in FIGS. 1A-1C, which can be grasped by a user to lift and replace the cover layer 4 as-needed. Optionally, the cover layer 4 may have a tab 13 extending laterally from an edge of the subjacent patch 1, presenting a gripping point where a user can easily grasp and lift the cover layer 4, and then reseat it. The tab 13 may have a textured surface to aid gripping it for manipulation of the cover layer 4. For example, the entire top surface of the cover layer may be textured.

The following will describe an exemplary method of applying an ECG electrode assembly as herein described. First, the patch 1 is applied to a patient's skin via a skin-compatible adhesive at its bottom surface. That adhesive typically is applied as a coating on the bottom surface, which can be exposed via removal of a disposable release liner (not shown). Next, referring to FIG. 1A, the button connector 3 is exposed by separating the cover layer 4 from the patch 1. Referring to FIG. 1B, the ECG lead wire 5 is secured to the button connector 3 via a lead wire clip 7. When the bottom surface of the cover layer 4 is adhesive-coated, an optional release liner (not shown) may be peeled away to expose the adhesive coating. Referring to FIG. 1C, the bottom surface of the cover layer 4 is then placed over the emplaced lead wire clip 7 as well as optionally a terminal portion of the lead wire 5 approaching that clip 7. When present, the adhesive on the bottom surface of the cover layer 4 secures the cover layer 4 to the top surface of the patch 1 surrounding the lead wire clip 7. Alternatively, when affixation between the cover layer and the patch is provided via tacky cohesion/adhesion, no release liner will be present and such affixation can be provided by pressing the opposing elements together, again securing them together surrounding the lead wire clip 7.

With the lead wire clip 7 secured to the button connector 3 and enclosed between the adhesive/cohesively affixed cover layer 4 and patch 1, a more robust connection of the lead wire clip 7 to the electrode connector 3 is realized. Specifically, the cover layer 4 helps resist extrinsic forces acting on or supplied through the lead wire 5 that may otherwise tend to draw the lead wire connector 7 out of engagement with the button connector 3. For example, when the patient moves or shifts in bed or otherwise ambulates, the lead wire 5 may catch or snag on external features such as posts, railings, furniture, etc., resulting in forces that would tend to disconnect the lead wire clip 7 from the button connector 3. However, when enclosed by the cover layer 4, which is separately affixed to the patch 1 surrounding and encasing that connection, the connection is reinforced such that forces exerted by the lead wire can be at least partially transferred to and absorbed by the cover layer 4. Accordingly, separation of the connection is resisted no longer merely by the snap-fit engagement between the lead wire clip and the button connector 3, but in addition by the cohesive/adhesive connection that affixes the cover layer 4 to the patch 1.

Figure 2A:
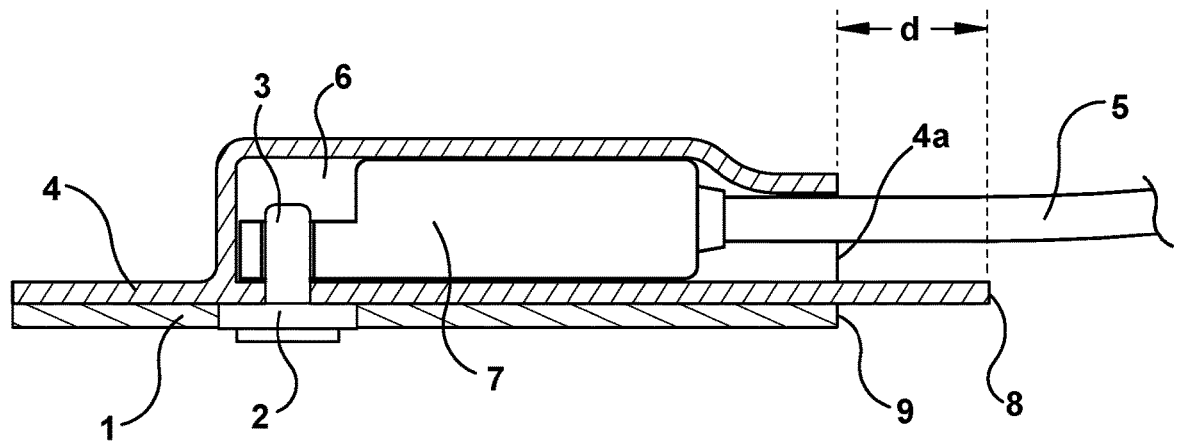
FIG. 2A illustrates a cross-sectional view of the first embodiment that includes a recess from its perimeter edge that is configured to accommodate a lead wire.
Figure 2B:
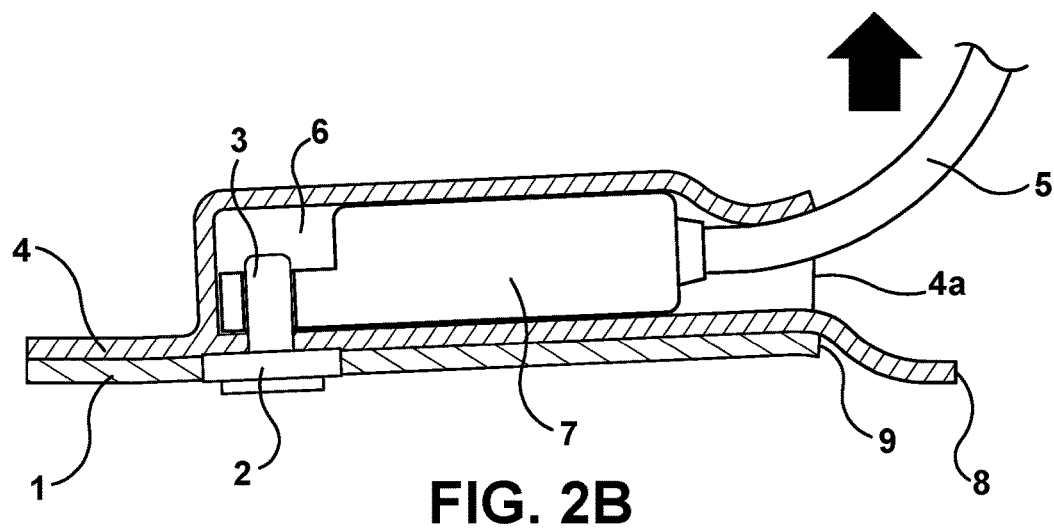
FIG. 2B illustrates another cross-sectional view of the embodiment of FIG. 2A when stress is applied to the lead wire.

Optionally, as shown in FIGS. 2A-2B, the cover layer 4 is of sufficient dimension to provide a terminal adhesive lip portion 8 extending beyond an edge 9 of the patch 1 about its perimeter when adhered thereto. For example, the distance between the edge 9 of the patch 1 and the edge of the terminal adhesive lip portion 8 is shown in FIG. 2A as d, which may be 1-20 mm. The terminal adhesive lip portion 8 of the cover layer 4 then can be adhered to the patient's skin surrounding the patch 1, which may further enhance the water-resistance thereof by protecting the adhesive connection between the patch 1 and the patient's skin. It also may help resist separation of the patch 1 from the patient's skin via unintended extrinsic forces applied via the lead wire 5. That is, stress is applied to the patch 1 when the lead wire 5 is pulled away from the patient. With the connection between that wire and the button connector 3 now reinforced as explained above, that stress will be more directly transferred to the patch 1 itself, which may be susceptible to removal from the patient's skin as a result. Extending the terminal adhesive lip 8 of the cover layer 4 beyond the edge 9 of the patch 1, so that the lip 8 itself is separately adhered to the patient's skin surrounding the patch, helps redirect the stress away from patch 1 itself, such that the entire assembly is more resistant to detaching from a patient when the lead wire 5 is pulled.

As shown in FIGS. 2A-2B and described above, the cover layer 4 defines a recess 6 that stands proud of the surrounding portion of that layer 4 and which is configured to accommodate the lead wire clip 7 therein. In this embodiment, cover layer 4 includes an access point 4a through which the lead wire 5 first penetrates the cover layer 4 and travels on its way to the lead wire clip 7 enclosed within the recess 6 thereof. Notably, that access point 4a is spaced inward of the edge of the terminal adhesive lip 8 of the cover layer 4 (e.g. by distance d) along the axis of the lead wire 5—meaning that the point where that lead wire 5 is first enclosed by the cover layer 4 also is so spaced. In this manner, if the lead wire 5 is tugged the resulting separation force will not be applied at the edge of the terminal adhesive lip 8 of the cover layer 4 (which may tend to peel it away). Rather, that force will be applied at a point recessed inward from that edge, wherein the cover-layer adhesion to the patient's skin will better resist the pulling force and protect the lead-wire connection to the electrode.

Figure 3A:
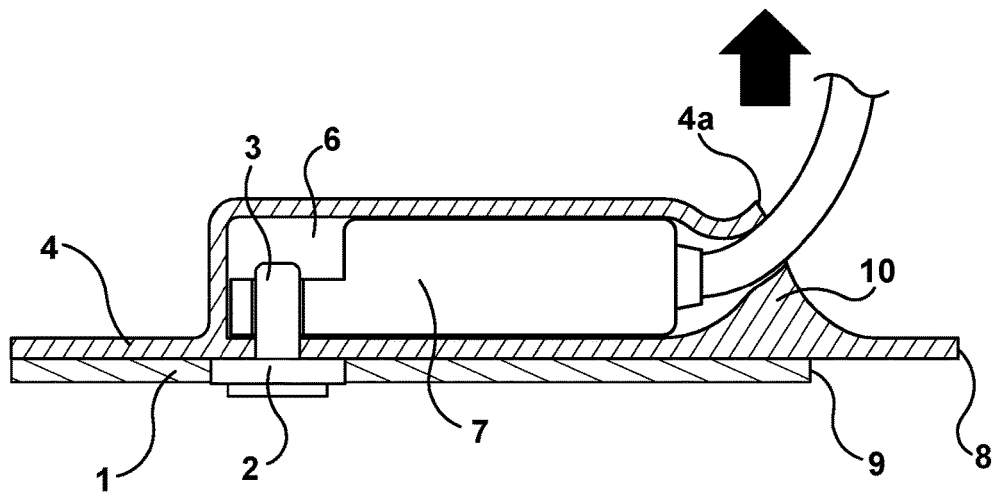
FIG. 3A illustrates a cross-sectional view of the first embodiment, wherein the cover layer includes an elastic portion in a vicinity where a lead wire approaches a button connector affixed to the patch, in order to provide strain relief for the lead wire.
Figure 3B:
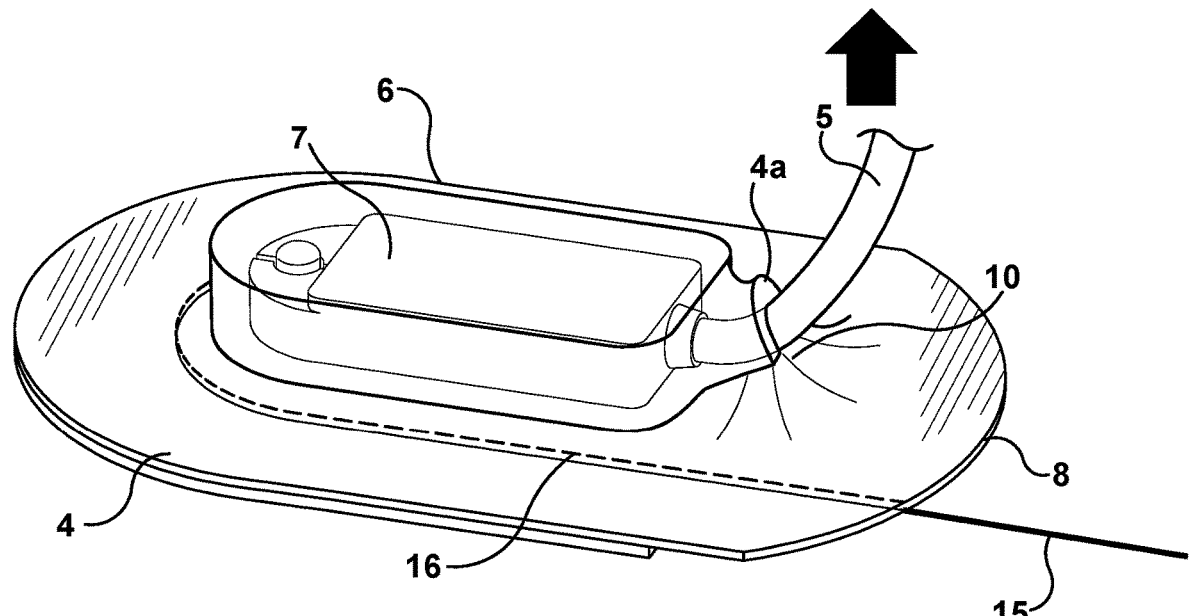
FIG. 3B shows a perspective view of the embodiment of FIG. 3A.

Moreover, as shown in FIGS. 3A and 3B, the cover layer 4 can include an elastic portion (e.g., a membrane) 10 in the plane of the cover layer 4 and disposed in the vicinity where the lead wire 5 approaches the lead wire connector 7 (i.e. adjacent to the aforementioned access point 4a). The elastic portion 10 acts as a strain relief to accommodate and absorb stresses that may be introduced as the patient moves against the tension in the lead wire 5 and helps to resist and absorb the associated stresses that may otherwise draw the lead wire 5 away from the electrode assembly.

Figure 3C:
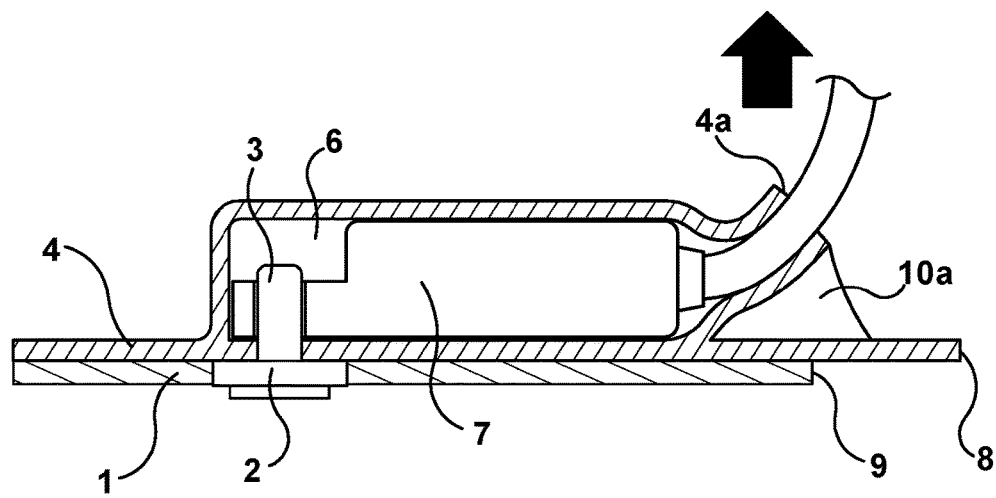
FIG. 3C illustrates a cross-section view of the first embodiment wherein the cover layer includes an elastic fin portion standing proud, as an alternative mechanism for providing strain relief for the lead wire.
Figure 3D:
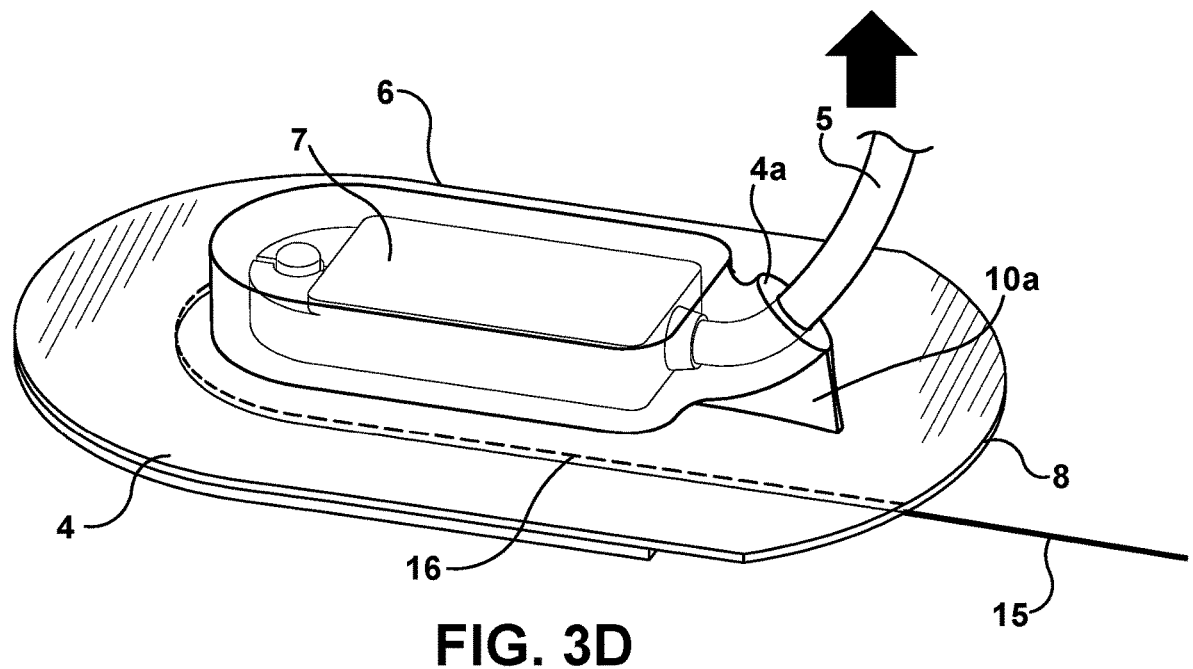
FIG. 3D shows a perspective view of the embodiment of FIG. 3C.

FIGS. 3C and 3D illustrate an alternative embodiment for providing strain relief against tension introduced via the lead wire 5. In this embodiment, the cover layer 4 includes an elastic fin 10a standing proud of the surrounding portion (e.g. planar expanse) of the cover layer 4, extending up to the access point 4a for the lead wire 5 where the latter penetrates the cover layer 4. This elastic fin 10a provides strain relief against tension 5 from the lead wire 5, wherein its flexure is adapted to absorb associated strain.

Figure 4:
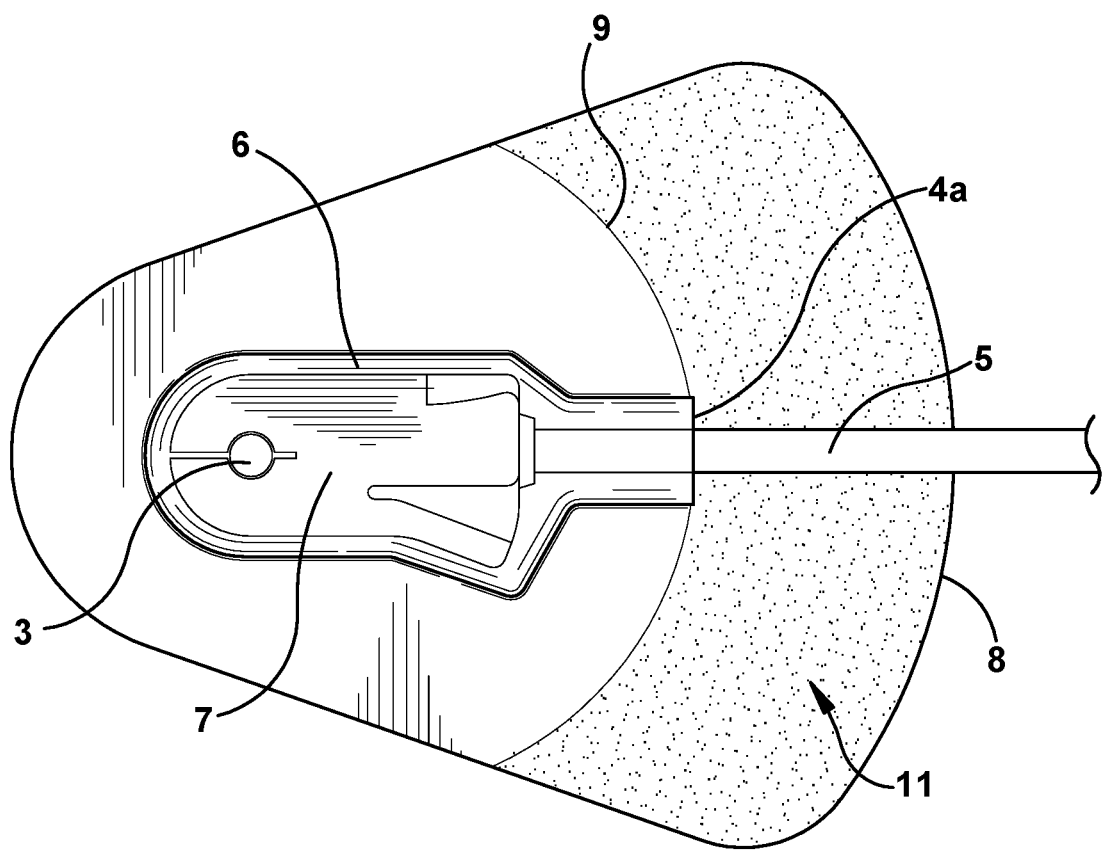
FIG. 4 illustrates a top view of the first embodiment where a terminal edge (e.g., a lip portion) of a cover layer extends substantially radially beyond an enclosure of the cover layer in the vicinity of an approaching lead wire.

Optionally, as shown in FIG. 4, the cover layer 4 can have an extended lip portion in the direction and vicinity of the approaching lead wire 5, extending a substantial distance radially beyond the recess 6 and the terminal edge 9 of underlying patch 1, as well as the access point 4a where the lead wire 5 penetrates the cover layer 4. This creates an extended adhesive attachment zone 11 between the cover layer 4 and the patient's skin in the vicinity of the approaching lead wire 5, and which adheres to the skin below the approaching wire. In the illustrated embodiment, the extended adhesive attachment zone 11 constitutes an annular segment of the cover layer 4 extending between the terminal edge 9 of the patch 1 and an edge of the lip portion 8 thereof, which is concentric with and disposed radially outward of the edge 9. This zone 11 provides a larger surface area of adhesive attachment between the cover layer 4 and the patient's skin in the vicinity where extrinsic forces will be introduced by tugging at the lead wire 5. This improved adhesion better resists tension stresses that otherwise might withdraw the wire 5 and produce a LEADS-OFF event.

In a further embodiment shown in FIGS. 5A and 5B, the patch 1 can have a plurality of electrodes and correspondingly a plurality of electrode contacts; i.e. respective button connectors 3. In the illustrated example, the patch 1 includes two electrode contacts (e.g. button connectors 3) spaced remote from one another, corresponding to remotely positioned electrodes adapted to detect cardiac electrical activity from different locations along the patient's body when the patch 1 is applied to the skin. In the illustrated embodiment, the two electrodes are spaced laterally. But other configurations and numbers of electrodes are possible. For example, the patch 1 can have three or more electrodes (and the associated electrode contacts) arranged in an array or at strategic locations corresponding to traditional ECG electrode-pickup locations along a patient's chest or back can be used. As shown, multiple ECG lead wires 5 can be attached to the patch 1 via respective lead wire clips 7 connected to the button connectors 3 for each electrode under a single, common cover layer 4. Alternatively, the ECG electrode assembly may include multiple cover layers (not shown), each configured to cover a single lead wire clip where it interfaces with a respective button connector 3. In either case, preferably the cover layer(s) 4 is/are all hingedly connected to the patch 1. For example, in FIG. 5A a single cover layer 4 is separated from the patch 1 to allow a user to connect a different lead wires 5 to each of the three button connectors 3. Once the lead wires 5 have been connected to the button connectors 3 via their respective lead wire clips 7, the user can manipulate the cove layer(s) 4 to cover those connections as shown in FIG. 5B.

Figure 6A:
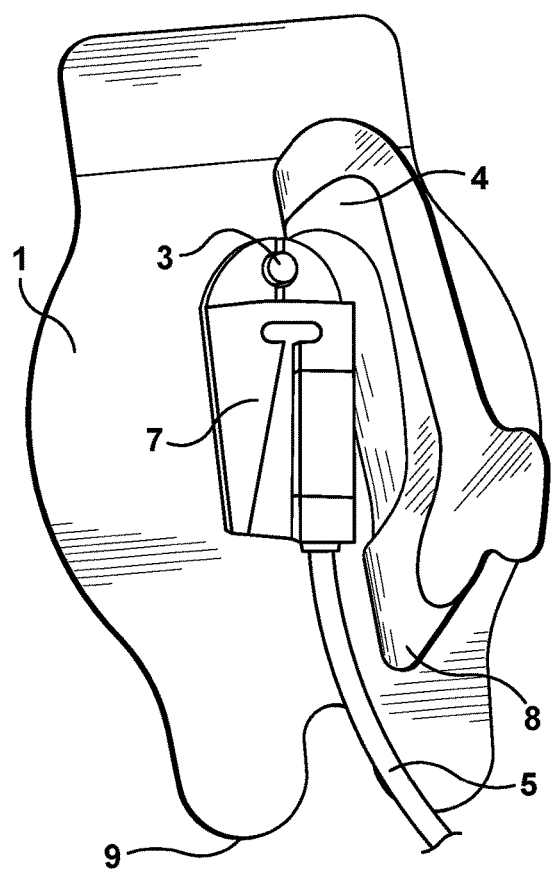
FIG. 6A illustrates a top view of a third embodiment of a disposable ECG electrode assembly having a cover layer configured to be substantially confined to a vicinity of a connected lead wire clip, wherein the cover layer is separated from an adhesive-backed patch.
Figure 6B:
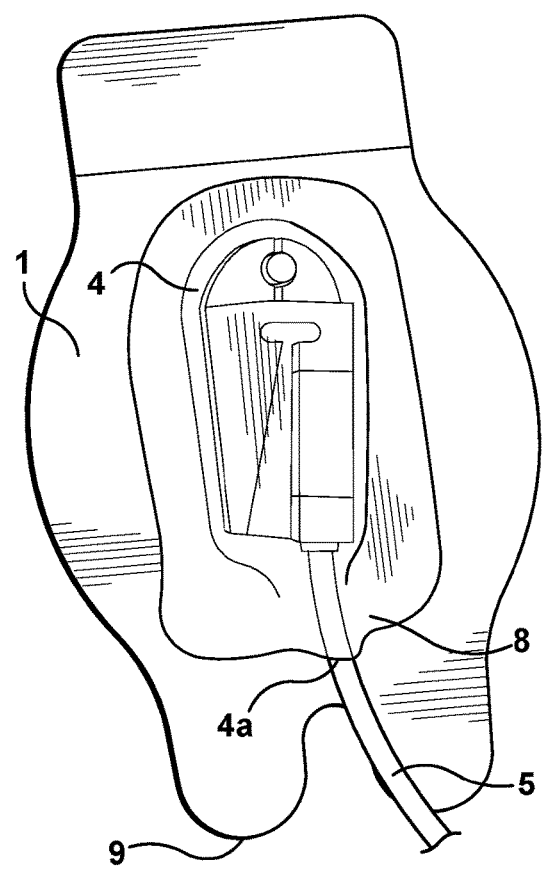
FIG. 6B illustrates a top view of the third embodiment after the cover layer has been placed over the connected lead wire clip, and secured to the adhesive-backed patch.

In a further embodiment illustrated in FIGS. 6A-6B, the ECG electrode assembly contains an adhesive-backed cover layer 4 configured to cover the lead wire clip 7 and a portion of the lead wire 5. But the cover layer 4 does not completely cover the underlying patch 1. Instead, the cover layer 4 has a smaller footprint than the underlying patch 1. Accordingly, when the cover layer 4 is secured to the top surface of the patch 1, the cover layer 4 is substantially confined to the vicinity of the lead wire clip 7 where it connects to the button connector 3 of the electrode, to cover and protect that connection. In the illustrated embodiment, the cover layer 4 covers the lead wire clip 7 where it attaches to the button connector 3, and a portion of that wire 5 leading to that clip 7. In this manner, the cover layer 4 can reinforce the lead wire 5 at a location adjacent to where it leads into the lead wire clip 7 beneath the cover layer. As above, the cover layer 4 protects the connection between the lead wire clip 7 and the button connector 3 and imparts water-resistance thereto, so that telemetry monitoring can be maintained while showering, so long as the adhesive that attaches the patch 1 itself to the skin is water resistant.

Any of the foregoing embodiments utilizing a cover layer 4 may include a rip cord 15 (see FIG. 3B) incorporated into or underlying the cover layer 4, extending beyond the terminal edge thereof. When it is desired to remove the lead wire 5 and dispose of the used ECG patch assembly, a user may pull the rip-cord to peel away (and optionally tear) the cover layer 4, thereby exposing the underlying lead wire connector 7 for easy detachment and removal from the patch 1. The rip cord can be a suture, string, wire, etc. integrated into the cover layer 4 or underneath it and adapted to tear away the cover layer 4 when pulled to expose the lead wire 5 and its lead wire connector 7 underneath. Optionally, the cover layer 4 may include a line of weakness 16 (e.g., via a linear series of perforations) along the path of the rip cord 15 to facilitate tearing the cover layer 4 along that path on pulling the cord 15. It will be appreciated that using the rip cord to tear the cover layer 4 along such a line of weakness typically would result in destructive removal of the cover layer 4 such that the entire assembly would thereafter be discarded.

Figure 7A:
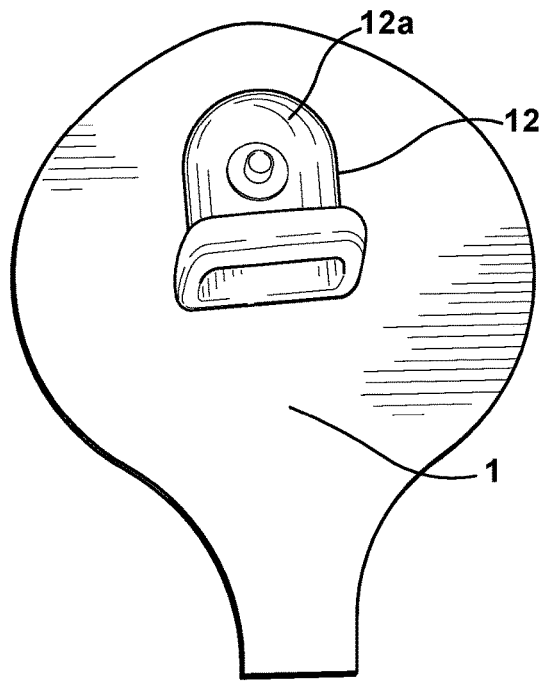
FIG. 7A illustrates a top view of a fourth embodiment of a disposable ECG electrode assembly having a cover sleeve configured to accommodate and be rolled over a connected lead wire clip when affixed to the electrode contact on the patch.
Figure 7B:
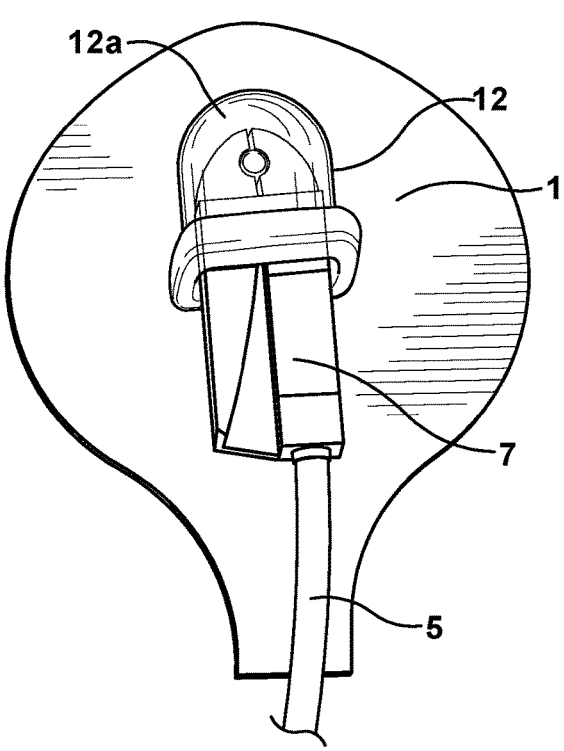
FIG. 7B illustrates a top view of the fourth embodiment where the cover sleeve has been partially rolled over a connected lead wire clip.
Figure 7C:
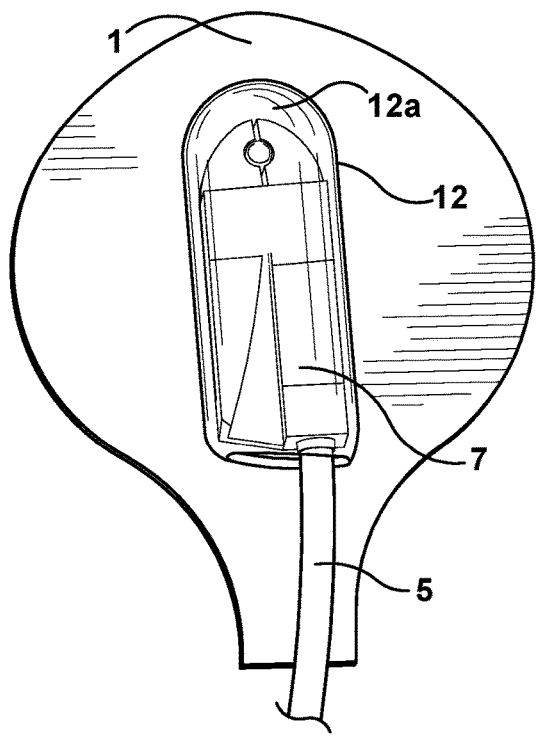
FIG. 7C illustrates a top view of the fourth embodiment where the cover sleeve has been completely rolled over the connected lead wire clip.

In yet a further embodiment illustrated in FIGS. 7A-7C, a cover sheath 12 can be affixed to the top surface of the patch 1 in the vicinity of the button connector 3. The cover sheath 12 is configured to roll over the lead wire clip 7 when connected to the button connector 3 on the patch 1, to thereby secure that connection and to provide water resistance thereto. As seen in FIG. 7A, the ECG electrode assembly is supplied with the cover sheath 12 rolled up over itself with a terminal portion 12a thereof available essentially as a socket for inserting the lead wire clip 7. The button connector 3 is disposed within that terminal portion 12, so that in-use the end of the lead wire clip 7 can be inserted into the terminal portion 12a and then secured (e.g. pressed down on) to the button connector 3. In use, the patch 1 is adhered to a patient's skin and the clip 7 of the lead wire 5 is then inserted within the terminal portion 12a of the sheath 12 and connected to the button connector 3. With the clip 7 and the lead wire 5 in place, the cover sheath 12 is unrolled over the clip 7 and the lead wire 5 to provide a protective barrier to that connection.

While ECG electrode assembly, including the associated patch 1 and cover layer 4 illustrated in foregoing embodiments are generally circular in shape, it is understood that any shape could be utilized (e.g., square, teardrop, etc.). In each of those embodiments, a cover layer is provided to help protect the ECG lead wire 5 and associated lead wire clip 7 at the point of attachment to the electrode contact (e.g. button connector 3) to reinforce that connection and improve retention of the ECG lead wire to the patch to minimize LEADS OFF failures. The cover layer also may provide water resistance to the patch assembly by protecting the connection between the lead wire 4 and the electrode thereof from water during normal ambulation and even bathing of a patient on monitor.

Any one of the foregoing features may be provided alone or in combination with any one or more of the other features discussed above. None of the disclosed features is to be considered mutually exclusive of any other unless their respective structures are expressly incompatible in the same electrode assembly.

Although the invention has been described with respect to select embodiments, it shall be understood that the scope of the invention is not to be thereby limited, and that it instead shall embrace all modifications and alterations thereof coming within the spirit and scope of the appended claims.

The invention claimed is:

1. An ECG electrode assembly comprising a patch incorporating a first ECG electrode, and a cover configured to cover and surround a first lead wire clip when attached to a first electrode contact of the first ECG electrode, said cover defining a recess therein that is dimensioned to accommodate the first lead wire clip when attached to the first electrode contact.

2. The ECG electrode assembly of claim 1, wherein the cover is integral to the patch.

3. The ECG electrode assembly of claim 1, wherein the cover is hingedly connected to the patch.

4. The ECG electrode assembly of claim 1, wherein a perimeter of the cover extends beyond a perimeter of the patch.

5. The ECG electrode assembly of claim 1, wherein the cover comprises a water-resistant material.

6. The ECG electrode assembly of claim 1, wherein the cover is configured to provide a substantially water-tight seal over the first lead wire clip attached to the contact.

7. The ECG electrode assembly of claim 1, further comprising a pressure-sensitive adhesive coating on a bottom surface of the cover layer at least partially surrounding said recess, said adhesive coating adapted to adhere the bottom surface of the cover layer to a top surface of said patch around said first lead wire clip.

8. The ECG electrode assembly of claim 1, said cover further comprising an elastic element disposed adjacent to an access point in the cover configured to accommodate said lead wire through the cover.

9. The ECG electrode assembly of claim 8, said cover comprising a cover layer, said elastic element comprising an elastic portion disposed in a plane of said cover layer.

10. The ECG electrode assembly of claim 1, further comprising a second ECG electrode incorporated into the patch and a second lead wire clip attached to a second electrode contact of the second ECG electrode, said cover being configured to cover and surround both the first lead wire clip and the second led wire clip.

11. The ECG electrode assembly of claim 10, the cover comprising a cover layer defining first and second recesses therein dimensioned respectively to accommodate the first and second lead wire clips attached to the first and second contacts, and a pressure-sensitive adhesive coating on a bottom surface of the cover layer at least partially surrounding both said first and second recesses, said adhesive coating adapted to adhere the bottom surface of the cover layer to a top surface of said patch around said first and second lead wire clips.

12. The ECG electrode assembly of claim 1, the cover further comprising a rip cord configured to at least partially separate the cover from the patch when pulled.

13. The ECG electrode assembly of claim 12, the cover comprising a cover layer having a line of weakness in a vicinity of said rip cord such that the cover layer will be torn along said line of weakness upon pulling the rip cord therethrough.

14. The ECG electrode assembly of claim 1, the cover further comprising a tab extending from a perimeter of the cover.

15. The ECG electrode assembly of claim 1, the cover comprising a cover layer having a textured surface.

16. The ECG electrode assembly of claim 1, wherein a bottom surface of the cover is releasably attached to a top surface of the patch surrounding said first lead wire clip.

17. The ECG electrode assembly of claim 16, wherein at least one of the top surface of the patch or the bottom surface of the cover layer possess(es) sufficient surface energy as to provide adhesive attachment therebetween based on their inherent tack.

18. The ECG electrode assembly of claim 17, said adhesive attachment being reversible.

19. An ECG electrode assembly comprising a patch incorporating a first ECG electrode, and a cover configured to cover and surround a first lead wire clip when attached to a first electrode contact of the first ECG electrode, said cover having a bottom surface facing the patch, an adhesive coating applied to the bottom surface of the cover, said adhesive coating comprising a pressure-sensitive adhesive.

20. The ECG electrode assembly of claim 19, said pressure-sensitive adhesive being a water-resistant pressure-sensitive adhesive.

21. An ECG electrode assembly comprising a patch incorporating a first ECG electrode and a second ECG electrode, a first cover configured to cover and surround a first lead wire clip attached to a first electrode contact of the first ECG electrode, and a second cover configured to cover and surround a second lead wire clip attached to a second contact of the second ECG electrode.

22. A cover comprising:
a bottom surface,
a top surface,
an adhesive disposed on the bottom surface, and
a recess defined in the cover and open from said bottom surface, the recess being dimensioned to accommodate a lead wire clip attached to a contact of an ECG electrode when the bottom surface is adhered to a patch comprising said contact.

* * * * *